(12) United States Patent
Thies et al.

(10) Patent No.: US 11,576,869 B2
(45) Date of Patent: Feb. 14, 2023

(54) DEVICE AND METHOD FOR GRANULATING, AGGLOMERATING, PELLETISING, DRYING AND/OR COATING

(71) Applicant: Glatt Maschinen- und Apparatebau AG, Pratteln (CH)

(72) Inventors: Jochen Thies, Loerrach (DE); Reinhard Nowak, Loerrach (DE)

(73) Assignee: Glatt Maschinen- und Apparatebau AG, Pratteln (CH)

( * ) Notice: Subject to any disclaimer, the term of this patent is extended or adjusted under 35 U.S.C. 154(b) by 0 days.

(21) Appl. No.: 17/357,195

(22) Filed: Jun. 24, 2021

(65) Prior Publication Data
US 2021/0315825 A1    Oct. 14, 2021

Related U.S. Application Data

(62) Division of application No. 15/971,228, filed on May 4, 2018, now Pat. No. 11,077,064.

(30) Foreign Application Priority Data

May 9, 2017   (DE) .......................... 102017109951.4

(51) Int. Cl.
*A61K 9/16*      (2006.01)
*A61K 9/20*      (2006.01)
(Continued)

(52) U.S. Cl.
CPC .......... *A61K 9/2893* (2013.01); *A61K 9/1682* (2013.01); *A61K 9/2095* (2013.01);
(Continued)

(58) Field of Classification Search
CPC .. A61K 9/2893; A61K 9/1682; A61K 9/2095; F26B 25/10; F26B 3/082;
(Continued)

(56) References Cited

U.S. PATENT DOCUMENTS 3,913,847 A    10/1975  Glatt et al.
4,511,093 A     4/1985  Ohkoshi et al.
(Continued)

FOREIGN PATENT DOCUMENTS

DE    2317129        10/1974
DE    2805397 A1      8/1979
(Continued)

*Primary Examiner* — Alexander M Weddle
(74) *Attorney, Agent, or Firm* — The Webb Law Firm

(57) ABSTRACT

Provided is a device for granulating, agglomerating, pelletising, drying and/or coating, the device including a swirl chamber, a distribution chamber, wherein the swirl chamber is separated from the distribution chamber by a base and wherein a powder to be granulated or a powder mixture to be granulated is presented in the swirl chamber, the device further including at least one agitator for thoroughly mixing the powder to be granulated or the powder mixture to be granulated and at least one addition device for a liquid, wherein the base is designed in several parts and at least one base part is horizontally and/or vertically displaceable, with the result that that the base becomes a distributor plate. Also provided is a method for granulating, agglomerating, pelletising, drying and/or coating using such a device and a base suitable for use as a distributor plate in a convective drying apparatus.

4 Claims, 3 Drawing Sheets

(51) Int. Cl.

| | |
|---|---|
| *A61K 9/28* | (2006.01) |
| *B01J 2/00* | (2006.01) |
| *B01J 2/10* | (2006.01) |
| *B01J 2/16* | (2006.01) |
| *F26B 25/10* | (2006.01) |
| *F26B 3/08* | (2006.01) |
| *F26B 3/092* | (2006.01) |

(52) U.S. Cl.
CPC ............... *B01J 2/003* (2013.01); *B01J 2/006* (2013.01); *B01J 2/10* (2013.01); *B01J 2/16* (2013.01); *F26B 3/082* (2013.01); *F26B 3/0926* (2013.01); *F26B 25/10* (2013.01)

(58) Field of Classification Search
CPC .. F26B 3/0926; B01J 2/006; B01J 2/16; B01J 2/003; B01J 2/10
See application file for complete search history.

(56) References Cited

U.S. PATENT DOCUMENTS

| | | | |
|---|---|---|---|
| 4,591,324 A | 5/1986 | Kubota | |
| 4,623,098 A | 11/1986 | Motoyama et al. | |
| 4,947,923 A | 8/1990 | Rikker | |
| 4,967,688 A | 11/1990 | Funakoshi et al. | |
| 6,492,024 B1 * | 12/2002 | Walter | B01J 2/16 241/27 |
| 6,949,141 B2 * | 9/2005 | Huttlin | B01J 8/44 118/62 |
| 2003/0180455 A1 * | 9/2003 | Maetani | B01J 2/16 427/127 |
| 2014/0263067 A1 | 9/2014 | Vaughan | |
| 2016/0074827 A1 | 3/2016 | Jacob et al. | |

FOREIGN PATENT DOCUMENTS

| | | |
|---|---|---|
| DE | 2924342 A1 | 11/1980 |
| WO | 2015117577 A1 | 8/2018 |

* cited by examiner

DEVICE AND METHOD FOR GRANULATING, AGGLOMERATING, PELLETISING, DRYING AND/OR COATING

CROSS-REFERENCE TO RELATED APPLICATIONS

This application is a divisional of U.S. patent application Ser. No. 15/971,228, filed May 4, 2018, which claims priority to German Patent Application No. 10 2017 109 951.4, filed May 9, 2017, the disclosures of which are hereby incorporated in their entirety by reference.

BACKGROUND OF THE INVENTION

The invention is based on a device and method for granulating, agglomerating, pelletising, drying and/or coating, in particular for the targeted production of multistage agglomerates.

Devices and methods for granulating, agglomerating, pelletising, drying and/or coating have been prior art for a long time. According to prior art, wet granulation is performed in so-called high-shear granulators. The subsequently required drying is carried out in convective driers such as fluidised-bed apparatus. As a result of the fact that two machines are required for this type of granulation, multistage granulation with intermediate drying steps is possible only at great space and investment costs.

The published patent application DE 28 05 397 A1 discloses a fluidised-bed apparatus with a horizontal rotor located above the distributor plate, wherein the rotor is arranged for vertical displacement in the upward-tapering fluidised-bed container, so that the flow conditions in the swirl chamber can be adapted to different granulates. This system has the disadvantage that the granulation and/or agglomeration cannot be carried out without simultaneous drying, because otherwise the granulates and/or agglomerates would fall from the rotor onto the distributor plate and the fluidised-bed apparatus would at least be greatly contaminated thereby.

In published patent application DE 2 317 129 A, a two-phase granulator is shown. The two-phase granulator consists of a container top part and a base part, and in the container the moistened mixture which is introduced is granulated by an agitator and dried by means of warm air which is fed in. For the warm air feed, the container top part has to be raised off the base part by a lifting device to form an air gap between the side wall of the container top part and the base part. The technical solution offered in this published patent application has the disadvantage that the lifting device is cost-intensive and the air gap provided thereby facilitates only an inadequate fluidisation of the granulated in the container.

An apparatus for the formation of granulates or agglomerates is disclosed in published patent application DE 29 24 342 A1. This apparatus comprises a container for mixing at least one solid and liquid material, which container is separated from a gas supply by a first tightly sealing base. For drying the mix thus formed by swirling in the container, the first tightly sealing base is replaced by a second base with gas through-openings, and the mixture is fluidised and dried by the drying gas flowing through the apparatus from the bottom towards the top. This system has the disadvantage that such an exchange of bases is very laborious. In addition, the base which is currently not used and which is stored outside the apparatus requires additional space. Furthermore, the exchange of the bases results in a different degree of drying, because the drying of the mix does not start simultaneously.

SUMMARY OF THE INVENTION

The invention is therefore based on the problem of developing a device for granulating, agglomerating, pelletising, drying and/or coating and a corresponding method which would overcome the disadvantages inherent in prior art.

This problem is solved by a device and method for granulating, agglomerating, pelletising, drying and/or coating and by a base with the features discussed herein.

The device according to the invention with the characteristic features discussed herein for granulating, agglomerating, pelletising, drying and/or coating, in particular for the provision of a targeted multistage granulation, which device comprises a swirl chamber, a distribution chamber, wherein the swirl chamber is separated from the distribution chamber by a base and wherein a powder to be granulated or a powder mixture to be granulated is presented in the swirl chamber, and which further comprises at least one agitator for thoroughly mixing the powder to be granulated or the powder mixture to be granulated and at least one addition device for a liquid, e.g. a nozzle or the like, for the addition of the granulating liquid, offers the advantage that a space- and cost-saving device is provided. Surprisingly, granulates analogous to those produced by a high-shear granulator could be produced by means of the present invention and dried in the same apparatus at varying air flow rates—e.g. in the fluidised bed—and then granulated further. The device according to the invention henceforth facilitates multistage granulation with intermediate drying steps of varying duration and frequency. A product transfer from the high-shear granulator to the device for convective drying, e.g. in the fluidised bed, can therefore be omitted. In the drying phase, e.g. in the fluidised bed or the like, the granulates, agglomerates or pellets can be coated using the at least one addition device for a liquid.

According to an advantageous embodiment of the device according to the invention, the at least one part of the base is only displaced horizontally and/or vertically within the device. This offers the advantage that the device can be made even more space-saving and therefore does not require additional space in contrast to a conventional granulator, in particular a high-shear granulator or the like. The device according to the invention therefore only requires the space of the granulator itself, in particular that of a high-shear granulator.

According to a further advantageous embodiment of the device according to the invention, the device comprises at least one drive unit with a speed range for the provision of a drive torque required for the agitator.

According to a further advantageous embodiment of the device according to the invention, the drive unit provides a consistently high drive torque throughout its speed range. This has the surprising result that the granulate properties, e.g. the granulate particle size or the like, of the product can be influenced and directly adjusted while the process is running. It has surprisingly been found that the provision of a consistently high drive torque by the drive unit throughout its speed range allows the shear forces, which are proportional to the agitator speed, to be changed or varied in the granulation process in such a way that the granulate properties, e.g. the granulate particle size or the like, can be adjusted directly. The torque in this context should be designated or understood to be the physical variable which generates a torsion or bending of the drive shaft. It is the product of force [N] and lever arm [m], as long as the force and the lever arm are perpendicular to each other. The torque has an energy unit of:

1 Nm (Newton metre) corresponds to 1 J (Joule) or 1 Ws (Watt second).

The torque of the drive shaft driving the agitator is proportional to the power output of the DC or AC motor coupled to the drive shaft.

$$P = 2 \cdot \pi \cdot M \cdot n$$

M: torque [Nm]
n speed [1/s]
P: power [W]
π: pi (3.1415926)

A further advantage of a consistently high drive torque made available by the drive unit is that the agitator can always mix the granulating mass, which may be very tough and viscous as a result of the addition of granulating liquid, thoroughly. The start of the agitator after a resting phase of the granulating mass can always be ensured as well as a result, although the granulating mass can become be very tough and viscous as a result of the addition of granulating liquid. The rest phase(s) during granulation is/are useful for many granulation processes and their products, because the granulating liquid as a rule requires some time for optimum interaction with the powder mixtures provided. In this, diffusion and swelling processes play an important role, and in addition the required amounts of granulating liquids can be reduced by the rest phase(s). The drive unit may for example be a hydraulic, servo and/or torque motor. All these drive units offer the advantageous feature that the torque which is generated can be controlled independently of speed, i.e. that the torque is consistent throughout the speed range. In addition, the device may comprise a chopper. The chopper chops lumps or pieces which have become too large owing to agglomeration processes, thereby additionally ensuring a precise adjustment of granulate particle size. The device moreover comprises a particle size measuring system. Such a particle size measuring system offers the advantage that it can ensure the monitoring of the granulate particle size, for example by using camera systems or the like, i.e. technical systems capable of detecting the granulate particle size. The particle size measuring system increases product quality and makes the granulation process independent of human monitoring if used. In addition, the device can comprise further measuring systems, which detect the properties of the granulate particles during the granulation process, for example, and can therefore influence them directly afterwards. Here, sensors are used among other things for detecting the temperature and/or humidity of the granulate and/or of the air. The additional measuring systems further enhance the quality of the granulate.

The method according to the invention with the characterising features discussed herein for granulating, agglomerating, pelletising, drying and/or coating, in particular for the provision of a targeted multistage granulation and/or agglomeration and/or pelletisation, which method comprises a swirl chamber, a distribution chamber, wherein the swirl chamber is separated from the distribution chamber by a base and wherein a powder to be granulated or a powder mixture to be granulated is presented in the swirl chamber, and which further comprises at least one agitator for thoroughly mixing the powder to be granulated or the powder mixture to be granulated and at least one addition device for a liquid, e.g. a nozzle or the like, for the addition of the granulating liquid, offers the advantage that, surprisingly, granulates analogous to those produced by a high-shear granulator can be produced using the method according to the invention and dried in the same apparatus at varying air flow rates—e.g. in the fluidised bed—and then granulated further. The method according to the invention henceforth facilitates multistage granulation with intermediate drying steps of varying duration and frequency. A product transfer from the high-shear granulator to the device for convective drying, e.g. in a fluidised bed, can therefore be omitted. The method steps, which run at least partially one behind the other, are all carried out in one and the same device. Any number of granulation and drying steps can be arranged in sequence in order to adapt the particles to be produced optimally to the desired requirements.

According to an advantageous embodiment of the method according to the invention, the powder introduced into and to be granulated in the at least one swirl chamber or the powder mixture introduced into and to be granulated in the at least one swirl chamber in the at least one granulation, pelletising and/or coating process is mixed by the at least one agitator while liquid is added at least intermittently. This advantageously makes for an optimum granulation step and provides an optimum granulate and/or agglomerate and/or pellet.

According to an additional advantageous embodiment of the method according to the invention, at least a part of the base is displaced horizontally and/or vertically during and/or after the at least one granulation, pelletising and/or coating process, with the result that the base becomes a distributor plate. If the base is changed to become a distributor plate, at least a partial drying process can advantageously run during the granulation process, for example. In addition, the granulates and/or agglomerates and/or pellets can be fluidised and dried in the fluidised bed. Following this drying process, a further granulation process can be carried out, for example. It is therefore possible to produce products with a different number of layers. During and/or after each granulation process, at least partial drying is therefore possible.

According to an additional advantageous embodiment of the method according to the invention, a gas flows via the distributor chamber through the swirl chamber in the drying or cooling process, whereby the granulates and/or agglomerates and/or pellets are fluidised. By varying the drying gases which at least partially fluidise and thereby dry the granulates and/or agglomerates and/or pellets, it is for example also possible to reduce germination by using or at least temporarily introducing special drying gases. Owing to the at least one addition device for liquid, it is furthermore possible to coat the granulates and/or agglomerates and/or pellets in the drying phase, e.g. in the fluidised bed or the like.

The base according to the invention with the characterising features of patent claim 9, which is also suitable for acting as a distributor plate in a convective drying apparatus, in particular in a fluidised bed apparatus or the like, offers the advantage that it becomes a distributor plate, so that in a likewise inventive device both a granulation and/or agglomeration process and a convective drying process can be carried out. Devices for displacing at least one base part are advantageously provided on the base according to the invention, so that the base according to the invention becomes a distributor plate, such devices preferably operating on an electric or hydraulic basis or the like or on a combination thereof.

Further advantages and advantageous developments of the invention can be gathered from the following description, the claims and the drawings.

BRIEF DESCRIPTION OF THE DRAWINGS

Preferred embodiments of the subject matter of the invention are shown in the drawing and explained in greater detail below. Of the drawing.

DESCRIPTION OF THE INVENTION

Figure 1:
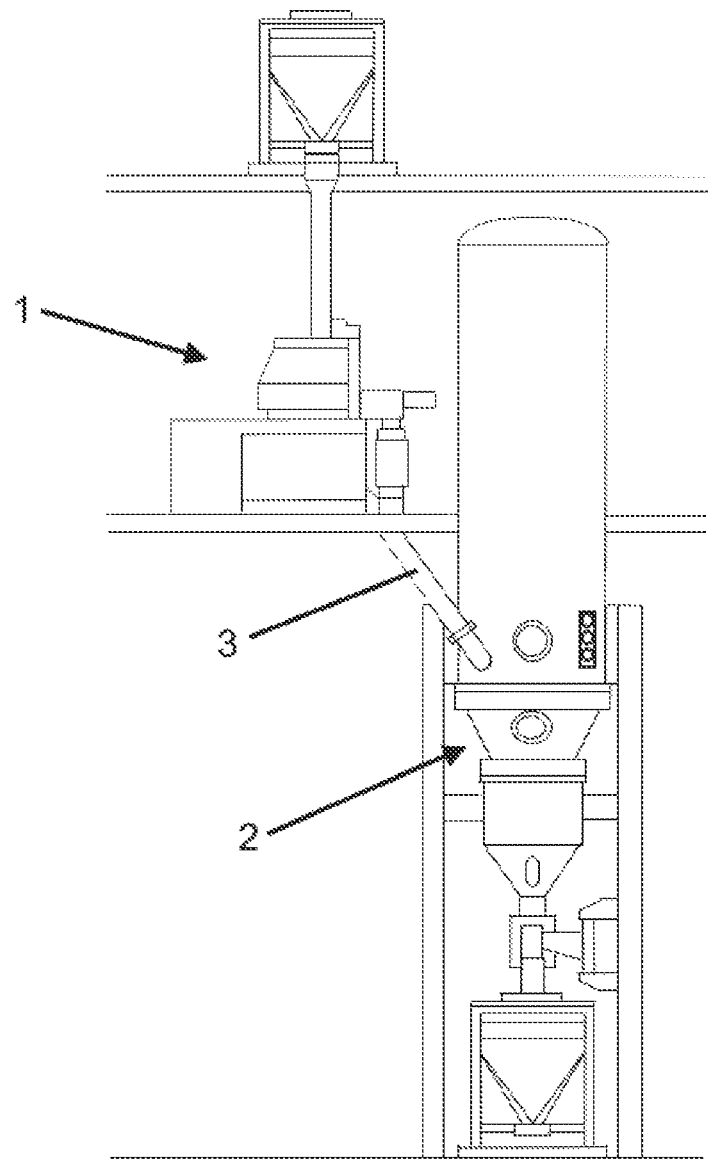
FIG. 1 shows a prior art device.

FIG. 1 illustrates prior art which consists of an arrangement of at least one granulator 1 connected in series in a cascade arrangement and a convective drier 2, e.g. in the form of a fluidised bed system. Via a conveying line 3, the granulator 1 and the convective drier 2 are connected in such a way that the granulate produced in the granulator 1 can be conveyed or transported into the convective drier 2 for after-treatment, in particular drying. Prior art therefore allows multistage granulation exclusively on the basis of a plurality of series-connected granulators 1 and convective driers 2. The method of prior art always requires the transfer of the moist granulate into the convective drier 2. In the simplest case, the granulate is transferred by providing that the convective drier 2—here a fluidised bed container—is placed below the outlet of the granulator 1, preferably a high-shear granulator or the like, resulting in a gravity-driven transfer of the granulate.

Figure 2:
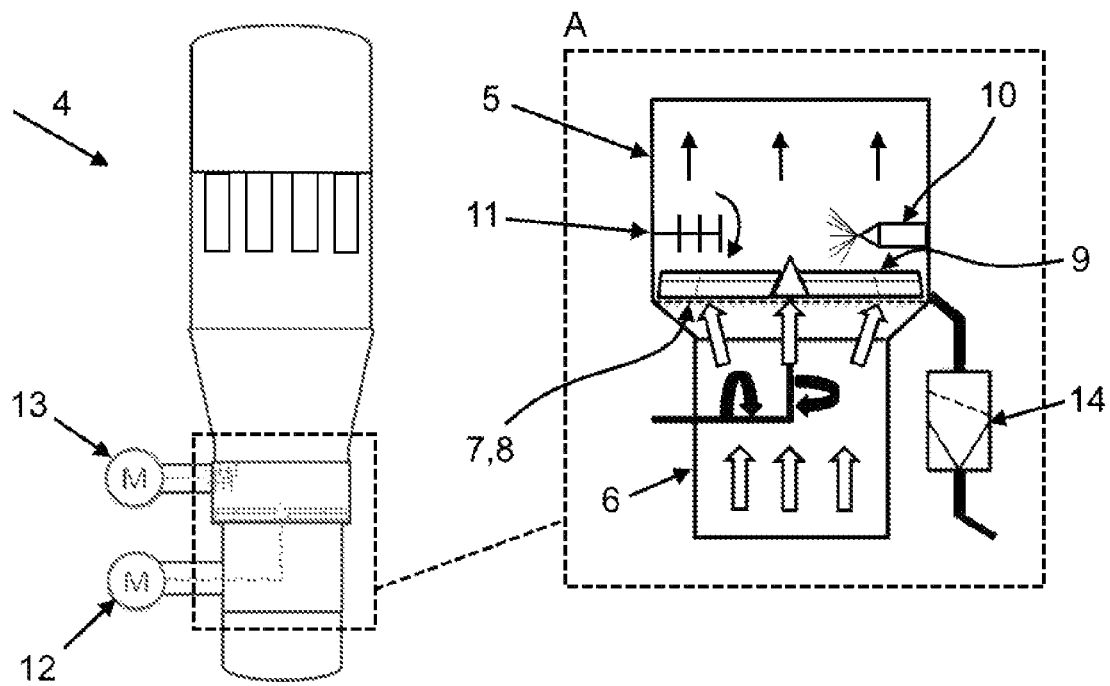
FIG. 2 is a diagrammatic representation of a device according to the invention.

FIG. 2 offers a diagrammatic representation of a device 4 according to the invention. A detailed view of the device 4 according to the invention is shown enlarged in section A. A swirl chamber 5 is located above a distributor chamber 6, the swirl chamber 5 and the distributor chamber 6 being separated from each other by a base 7 according to the invention, The base 7 according to the invention is impermeable to liquids, solids and/or gases. In addition, the base 7 according to the invention is a multi-part component, i.e. the base 7 according to the invention comprises at least two base parts. At least one base part of the multi-part base 7 according to the invention is horizontally and/or vertically displaceable. The term "displaceable" here means that at least one base part is slidable and/or twistable and/or pivotable and/or rotatable or the like. By displacing at least one base part of the base 7 according to the invention, the base 7 becomes a distributor plate 8. In contrast to the base 7, the distributor plate 8 is permeable to liquids, solids and/or gases. The horizontal and/or vertical displacement of at least one base part results in openings in the base 7, so that liquids, solids and/or gases can pass through the base 7. To fluidise the granulate produced on the base 7 according to the invention, at least approximately 5% of the area of the base 7 according to the invention should be open, producing the distributor plate 8. In the swirl chamber 5, at least one agitator 9 for thoroughly mixing and/or granulating at least one presented powder is arranged above the base 7 according to the invention. The at least one powder is fed in via a feed device (not shown here) of the device 4 according to the invention.

Furthermore, above the base 7 according to the invention, at least one device 10, such as a nozzle or the like, for adding a liquid, in particular a granulating liquid, and a chopper 11 are located. The at least one liquid addition device 10 furthermore offers the opportunity for coating the granulates, agglomerates and/or pellets. In the food and pharmaceutical industries, coating is used for products such as granulates, agglomerates and/or pellets or the like. The coating process for particles is always used when the surface properties of the raw products are to be modified, e.g. when the raw products have to be protected in some way. By coating, the surface can be made hydrophobic or sealed, for example. In the pharmaceutical sector special coatings are used to produce so-called retard preparations, whose action principle is based on the retarded release of active ingredients. Not least, coating is also used to influence the taste of a product—for example by applying a sugar layer which masks the bitter taste of drugs. The agitator 9 is for example placed above a shaft located centrally in the device 4 according to the invention and is preferably driven by means of a drive unit 12. The drive unit 12 provides the drive torque required for the agitator 9. The drive unit 12 can provide a consistently and/or inconsistently high drive torque throughout its entire speed range. By the consistently high torque of the drive unit 12, the granulate properties, such as the granulate particle size or the like, of the product can surprisingly be influenced and directly adjusted while the process is running. The provision of a consistently high torque by the drive unit 12 throughout its entire speed range allows the shear forces, which are proportional to the agitator speed, to be changed or varied in the granulation process in such a way that the granulate properties, such as the granulate particle size or the like, can be adjusted directly. The torque in this context should be designated or understood to be the physical variable which generates a torsion or bending of the drive shaft. It is the product of force [N] and lever arm [m], as long as the force and the lever arm are perpendicular to each other. The torque has an energy unit of:

1 Nm (Newton metre) corresponds to 1 J (Joule) or 1 Ws (Watt second).

The torque of the drive shaft driving the agitator 9 is proportional to the power output of the DC or AC motor coupled to the drive shaft.

$$P = 2 \cdot \pi \cdot M \cdot n$$

M: torque [Nm]
n speed [1/s]
P: power [W]
π: pi (3.1415926)

A further advantage of the consistently high torque provided by the drive unit 12 is that the agitator 9 can always mix the granulating mass, which can be very tough and viscous as a result of the addition of granulating liquid, very thoroughly. The start of the agitator 9 after a resting phase of the granulating mass can always be ensured as well as a result, although the granulating mass can become be very tough and viscous as a result of the addition of granulating liquid. The rest phase(s) during granulation is/are useful for many granulation processes and their products, because the granulating liquid as a rule requires some time for optimum interaction with the powder mixtures provided. In this, diffusion and swelling processes play an important role, and in addition the required amounts of granulating liquids can be reduced by the rest phase(s). The drive unit 12 may for example be a hydraulic, servo and/or torque motor. The chopper 11, which is driven by a further drive unit 13, chops lumps or pieces which have become too large owing to agglomeration processes, thereby additionally ensuring a precise adjustment of granulate particle size. In this way, a granulation can take place in the swirl chamber 5 above the base 7 according to the invention. During and/or after the granulation of the at least one powder presented in the swirl chamber 5, at least one base part of the base 7 can be displaced horizontally and/or vertically, turning the base 7 into a distributor plate 8. Through the distributor plate 8, a drying gas routed across the distributor chamber 6 enters the swirl chamber 5 for drying the granulate particles or agglomerates. As shown here in FIG. 2, this drying process can for example be carried out in a fluidised bed. After any number of granulation and drying processes in the device 4 according to the invention, the product is discharged via a discharge device not shown here. The product can then be routed through a sieve 14 for further increasing product quality. In the device according to the invention, e.g. the high-shear granulators described above, pellets, in particular round and evenly sized agglomerates, can be produced as well. A torque-stable mode of operation can also be advantageous for the shaping of the round agglomerates. As soon as the pellets are formed, an irregular growth process can be stopped or at least significantly delayed, e.g. by drastically reducing the agitator speed.

With the device 4 according to the invention and the method according to the invention, granulation processes which are not feasible using conventional prior art such as shown in FIG. 1 can be run.

Example 1: Granulation in Several Stages

In a first, upstream granulation process, small granulates are produced and then dried in a first drying process. In the following second granulation step, these granulates are granulated further, e.g. with a granulation medium having delayed release properties. This methodology allows the free configuration of the release behaviour of drugs. The process can be repeated with any frequency. In addition, it is also possible to produce the initial granulate with release-delaying granulating means.

Example 2: Production of Multiphase Granulates

A presented powder or a presented powder mixture is classically granulated in a first granulation process by adding a binding agent and then dried in a first drying process and thereby stabilised. A further powder or powder mixture is then introduced into the granulator and again granulated by adding a binding agent. The newly added powder now accumulates mainly around the existing granulate particles. In this way, granulates consisting of or having different layers—or phases—can be produced. By producing a three-phase granulate, for example, it is possible to process two active ingredients (one in the first phase and one in the third phase) to produce a dosage form in which the active ingredients must not come in contact with one another.

Example 3: Production of Very Large and Uniform Granulates

With the method described in prior art, it is not possible to produce large granulate structures in one device, because the drying process, e.g. in the fluidised bed or the like, runs from the outside to the inside. If the granulate is too large, effective drying is not possible, because the moisture or the solvent has to be diffused to the surface through the already dry outer layer. In the method and the associated device according to the invention large granulate structures can be produced similar to the production of the multiphase granulates (example 2) by repeated granulation and intermediate drying. By the intermediate drying of small granulate structures, an optimum drying process and thus an optimum structure of the granulate particles is always ensured.

Example 4: Production of Pellets from Powder and Solvent

In classic high-shear granulation, a binding agent dissolved in a solvent is usually added. According to the method described above, pellets can also be produced directly from powder by selecting suitable process conditions, e.g. high agitator speeds and a slow addition of binding agent. The classic production method involves the problem that the growth process has to be stopped at a specific point in time when the target size of the pellets is reached, and this can only be achieved by quick drying. For this purpose, the pellets have to be transferred into the fluidised bed, which in turn can result in damage to the still moist and fragile pellets. Furthermore, the transfer takes too much time, so that there is still further growth for a certain time. With the device and/or the method according to the invention, the drying process can be initiated very fast and gently, so that the growth process of the pellets can be stopped very quickly. By the displacement of at least one base part, the base according to the invention becomes a distributor plate. This facilitates the flow of a drying gas, e.g. air or the like, through the pellet bed, and the growth of the pellets is stopped immediately.

Example 5: Production of Pellets from Powder Without Solvent

With classic high-shear granulators, pellets can also be produced by melting a component of the powder mixture. Here, too, it is essential that pellet growth is stopped at a defined point in time, which in this case has to be achieved by cooling. However, a cooling process, e.g. owing to the jacket which has to be heated and/or cooled, takes far too much time. For the necessary fast cooling, dry ice and/or liquid nitrogen is/are therefore introduced directly into the pellet mass. In this process, fast and uniform distribution is difficult to ensure. In contrast to the classic method described above, uniform cooling can easily be obtained with the device, the base and the method according to the invention by providing that a suitably cold process air flows through the distributor plate produced from the base according to the invention by displacing at least one base part, thereby ensuring an optimum cooling of the pellets.

Example 6: Coating of Pellets

Pellets such as produced in examples 4 and 5 are often coated with release-delaying layers for the targeted control of the release of their active ingredients. With the device and/or the method according to the invention, the pellets can be coated immediately after drying and/or cooling in the same working container. The coating process can be accompanied by simultaneous air drying if the coating material is dissolved or suspended in a suitable solvent. If the base is closed, the pellets can also be coated with powder which is distributed evenly by the agitator.

All of the products produced in the above examples can at any time be subjected to a coating process which entails the advantages of the coating of particles as listed above.

Figure 3:
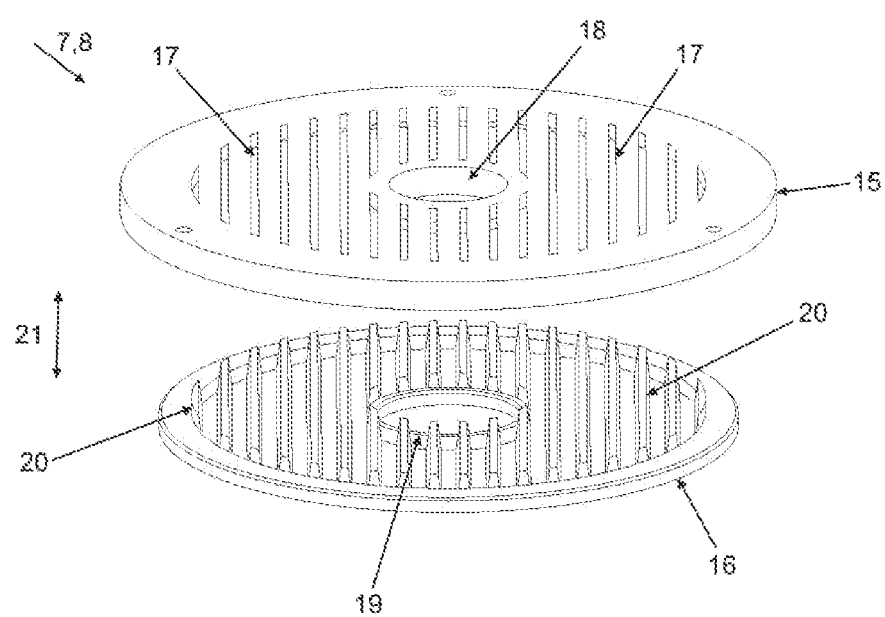
FIG. 3 is a perspective representation of a first embodiment of the distributor plate according to the invention.

FIG. 3 shows a first embodiment of a base 7 according to the invention, which in the device 4 according to the invention is preferably located between the swirl chamber 5 not shown here and the distributor chamber 6 not shown here. In the embodiment shown in FIG. 3, the base 7 according to the invention consists of a first, upper base part 15 and a second, lower base part 16. The first, upper base part 15 has openings 17 in the form of slots or the like. The openings 17 can vary in number and/or shape and/or position. In the illustrated embodiment, the first, upper base part 15 furthermore has a central opening 18 for the passage of the drive shaft (not shown here) of the agitator 9. In the device 4 according to the invention, several agitators 9 can be arranged on the base 7 according to the invention, so that the base 7 according to the invention may have further, non-central openings for the corresponding drive shafts. The second, lower base part 16 of the base 7 according to the invention has, in addition to a central opening 19, webs 20 which complement the openings 17. The webs 20 always match the openings 17 in number and/or shape and/or position, so that the openings 17 can be closed tightly by the webs 20. If, for example, the first, upper base part 15 and the second, lower base part 16 are aligned relative to each other as indicated by arrow 22 in the vertical direction, the base 7 according to the invention is in the first embodiment either closed, so that solids, liquids and/or gases cannot pass through, or the base 7 according to the invention becomes a distributor plate 8, so that solids, liquids and/or gases can pass through (open position—distributor plate 8—shown in FIG. 3). The first, upper base part 15 is preferably in a fixed location in the device 4 according to the invention. If the second, lower base part 16 of the base 7 according to the invention is in its upper starting position, the base 7 according to the invention is closed and the granulation process can run in the swirl chamber 5 above the base 7 according to the invention. If the second, lower base part 16 of the base 7 according to the invention is moved to a low position, however, the base 7 according to the invention becomes a distributor plate 8. Through this distributor plate 8, the gases, in particular drying gases or the like, can now flow to dry the granulate particles produced in the granulation process, e.g. in a fluidised bed. The flow rate of the gases, preferably of the drying gases or the like, always has to be adapted to the drying process. As soon as the drying process is finished, the second, lower base part 16 of the base 7 according to the invention can once again be joined to the first, upper base part 15 of the base 7 according to the invention. e.g. for a second granulation process or for discharge, so that the distributor plate 8 becomes the closed base 7 according to the invention. The granulation processes and the drying processes can be repeated optionally until an optimum product is made.

Figures 4A, 4B:
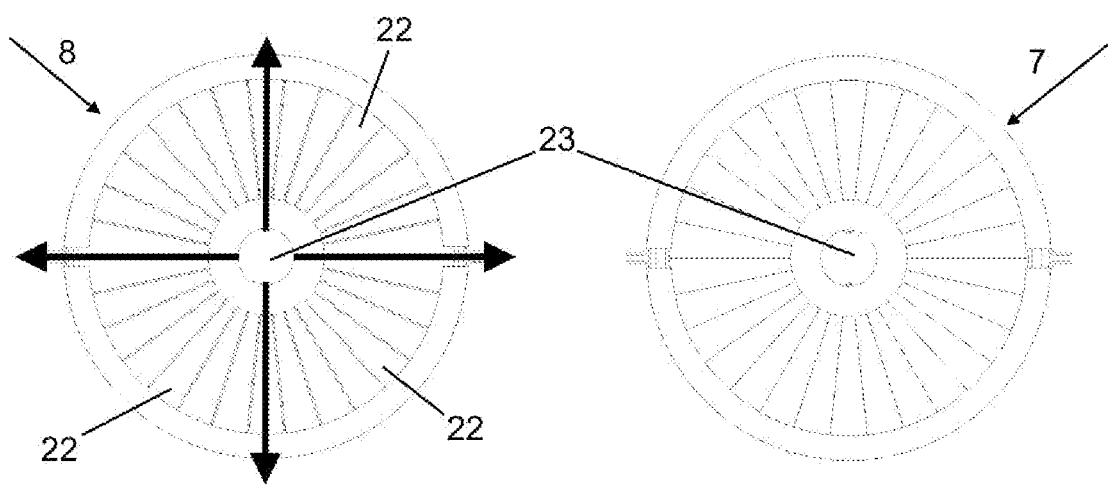
FIGS. 4(a) and 4(b) are top views of a second embodiment of the distributor plate (FIG. 4(a)) according to the invention and of the base (FIG. 4(b)) according to the invention.

FIGS. 4(a) and 4(b) show a second embodiment of the base 7 according to the invention. The base 7 according to the invention comprises a plurality of base parts 22, by means of which it is possible to turn the base 7 according to the invention (FIG. 4b) into a distributor plate 8 (FIG. 4a). The at least one base part 22 is here horizontally and/or vertically displaceable. To produce the distributor plate 8 (FIG. 4a) from the base 7 according to the invention shown in FIG. 4b, the at least one base part 22 is displaced horizontally and/or vertically, so that e.g. drying gases can pass through the distributor plate 8. In the second embodiment, the base parts 22 are displaced radially outwards in the direction of the arrows, turning the base 7 according to the invention (FIG. 4b) into a distributor plate 8 (FIG. 4a). The total displacement of the existing base parts 22 only has to be chosen such that the drying process, e.g. by fluidisation of the granulates and/or agglomerates, is optimal. The base 7 according to the invention of this embodiment likewise has a central opening 23 for the drive shaft of an agitator 9 not shown in the drawing.

All of the features specified here can be essential to the invention both individually and in any combination.

LIST OF REFERENCE NUMBERS

1 Granulator
2 Drier
3 Conveying line
4 Device
5 Swirl chamber
6 Distributor chamber
7 Base
8 Distributor plate
9 Agitator
10 Device for addition of a liquid
11 Chopper
12 Drive unit
13 Drive unit
14 Sieve
15 Base part
16 Base part
17 Opening
18 Central opening
19 Central opening
20 Web
21 Arrow
22 Base part
23 Central opening

The invention claimed is:

1. A method for granulating, agglomerating, pelletizing, drying and/or coating, comprising:
at least one granulation process and at least one drying process, the at least one drying process proceeding during and/or at least partially after the at least one granulation process,
wherein the method is performed using a device comprising:
a swirl chamber, wherein a powder to be granulated or a powder mixture to be granulated is presented in the swirl chamber;
a distributor chamber, wherein the swirl chamber is separated from the distributor chamber by a base;
at least one agitator for thoroughly mixing the powder to be granulated or the powder mixture to be granulated; and
at least one nozzle for a liquid,
wherein the base comprises at least two base parts; and
wherein at least one base part is horizontally and/or vertically displaceable between a first position wherein the base is impermeable to liquids, solids and/or gases and a second position wherein the base becomes a distributor plate that is permeable to liquids, solids and/or gases.

2. The method according to claim 1, wherein the powder introduced into and to be granulated in the swirl chamber or the powder mixture introduced into and to be granulated in the swirl chamber in the at least one granulation process is mixed by the at least one agitator while liquid is added at least intermittently.

3. The method according to claim 1, wherein at least one base part is displaced horizontally and/or vertically during and/or after the at least one granulation process, with the result that the base becomes the distributor plate.

4. The method according to claim 1, wherein a gas flows via the distributor chamber through the swirl chamber in the drying process, whereby granulate particles or pellets are fluidised.

\* \* \* \* \*